United States Patent [19]
Malmgren

[11] 3,990,066
[45] Nov. 2, 1976

[54] WATER QUALITY MONITOR

[76] Inventor: Arthur L. Malmgren, 386 NW. 112th St., Seattle, Wash. 98177

[22] Filed: Oct. 25, 1974

[21] Appl. No.: 517,854

[52] U.S. Cl. .............................. 340/285; 340/253 Y; 324/65 R; 324/DIG. 1; 210/85; 210/321 R; 323/75 N; 328/133
[51] Int. Cl.² ................... G08B 21/00; B01D 35/00
[58] Field of Search ............... 340/285, 420, 253 Y; 210/14, 96 R, 96 M, 85, 321; 324/58.5 A, 65 R, 71 CP, 33, DIG. 1; 328/208, 133, 134; 323/75 N, 75 R; 307/3, 20, 127, 26

[56] References Cited
UNITED STATES PATENTS

| | | | |
|---|---|---|---|
| 3,639,824 | 2/1972 | Malauaji | 323/19 |
| 3,652,910 | 3/1972 | Urbain | 210/96 |
| 3,838,774 | 10/1974 | Dolan et al. | 210/85 |
| 3,845,657 | 11/1974 | Hall et al. | 340/285 |

Primary Examiner—John W. Caldwell
Assistant Examiner—William M. Warnisky
Attorney, Agent, or Firm—Seed, Berry, Vernon & Baynham

[57] ABSTRACT

An apparatus for monitoring the performance of a reverse osmosis water purification system. The resistivity of the water, and hence its dissolved ionic material concentration, is measured at both the inlet and product ports of the system by resistance sensors forming two legs of a wheatstone bridge. The bridge is powered by two oppositely phased AC signals. The output of the bridge drives a phase sensitive null detector which generates a null error signal. After thresholding, the null error signal actuates a bidirectional meter to indicate the degree of bridge unbalance, as well as to actuate an alarm circuit if the outlet resistance falls below a predetermined value, thereby indicating an unacceptable degree of purification. The bridge is balanced by a potentiometer forming a pair of bridge legs on each side of the potentiometer wiper. Thus, when the bridge is balanced, the setting of the potentiometer wiper corresponds to a given ratio of inlet resistance to outlet resistance. This ratio corresponds to the percentage of ionic material in the product water which has been rejected from the inlet water. The potentiometer dial is calibrated in percent rejection, thereby giving an indication of the performance of the reverse osmosis water purification system. Means are also provided for actuating an alarm when the percent rejection falls below a predetermined value and for reading directly the resistivity, and hence ion concentration, of both inlet and product water.

17 Claims, 2 Drawing Figures

3,990,066

WATER QUALITY MONITOR

BACKGROUND OF THE INVENTION

1. Field of the Invention

This invention relates to phase sensitive null detectors and, more particularly, to such detectors used to measure the ratio of the resistivity of water entering a reverse osmosis water purifier to the resistivity of product water leaving a reverse osmosis water purifier.

2. Description of the Prior Art

Reverse osmosis water purification systems are in common use for removing ionic material dissolved in water. These systems generally comprise an enclosed container having input and output ports separated by a semi-permeable membrane, such as cellophane.

As is well known in the art, semi-permeable membranes have the characteristic of equalizing the concentration of metallic ions dissolved in a solvent on either side of the membrane. Thus, if the concentration of ions in a solvent, such as water, is greater on one side of the membrane than on the other, water will pass through the membrane from the side of lesser ion concentration to the side of greater ion concentration. The force causing water to move through the semi-permeable membrane in this manner is frequently referred to as osmotic pressure.

The flow of water that occurs through osmotic pressure can be reversed by increasing the pressure on the fluid on the side of greater concentration. In this manner, water can be forced through the membrane, leaving behind the metallic ions dissolved therein. Under these circumstances, the semi-permeable membrane acts essentially as a filter for separating the metallic ions from the water in which they are dissolved. This is the principle used in reverse osmosis water purification systems.

It is important to be able to measure the performance of such reverse osmosis water purification systems to insure that the water produced is of sufficient quality. The concentration of metallic ions in water is inversely proportional to the resistance of the water. Thus, the concentration of metallic ions in water can be calculated by measuring the resistance of the water. Such systems are well known and are in common use. However, since reverse osmosis water purification systems normally remove a relatively constant percentage of the dissolved ionic material, the ionic concentration considered acceptable at the product port will vary, depending upon the ionic concentration at the inlet port. In order to determine whether a purification system is operating properly, it is necessary to measure the resistances at both the inlet port and the product port, and to further calculate the percentage of dissolved ionic material being removed. This is basically how prior art water quality monitors function.

Prior art water quality monitors, as described above, are unacceptable for several reasons. First, insofar as a calculation must be made after each reading, instantaneous performance readings are not possible. Second, the calculation requirement dictates that the water quality monitor be manually operated, thereby increasing the cost of making such measurements. Because of the aforementioned disadvantages of prior art water quality monitors, there is a great need for such a monitor which will produce a signal indicative of the percentage of ionic material removed directly from resistivity measurements at the inlet and product ports.

SUMMARY OF THE INVENTION

It is an object of the present invention to provide a water quality monitor which will provide a visual indication of the percentage of metallic ions removed from water in a water purification system directly from resistivity measurements of the inlet water and product water.

It is another object of the present invention to provide a water quality monitor which will also allow measurement of the absolute concentration of metal ions dissolved in the water entering the purification system as well as the product water leaving the purification system.

It is still another object of the present invention to provide a water quality monitor that will actuate an audible or visual alarm to indicate that the performance of the purification system has fallen to a predetermined value.

It is a still further object of the present invention to provide a resistivity measurement circuit which uses a novel phase sensitive null detector to determine the resistivity ratio.

These and other objects of the present invention are accomplished by providing a resistivity sensor at both the inlet and product outlet fluid ports. The resistivity sensors form two legs of a wheatstone bridge, the remaining two legs of which are formed by the resistance on each side of a potentiometer wiper. The wheatstone bridge feeds a null detector, and the bridge is balanced by adjusting the potentiometer wiper. For any given resistance ratio of the resistivity sensors, the bridge can be balanced by adjusting the potentiometer wiper. When the bridge is balanced, the position of the potentiometer wiper will give an indication of the resistance ratio and hence the percentage of metallic ions which have been rejected from the inlet water in passing through the semi-permeable membrane. The potentiometer wiper rotates along a circular path and the angular position of the potentiometer shaft is compared to a fixed scale which is calibrated in percentage of ions removed.

The water quality monitor employs a novel null detector which is essentially a phase sensitive discriminator. The wheatstone bridge, which is powered by two oppositely phased AC signals, drives an operational amplifier having an output which is thresholded and fed to a switching circuit. The switching circuit is powered by the same two oppositely phased AC signals that power the wheatstone bridge. The switching circuit includes two current paths, each deflecting a meter in opposite directions. A comparison is made between the threshold output voltage and the two AC signals in order to determine through which of the current paths current will be allowed to flow. Since each of the current paths drives the meter in opposite directions, the position of the needle in the meter is an indication of the relative current flow through each of the current paths.

A circuit is also provided for actuating an alarm if the bridge circuit unbalances a predetermined amount.

DETAILED DESCRIPTION OF THE INVENTION

Figure 1:
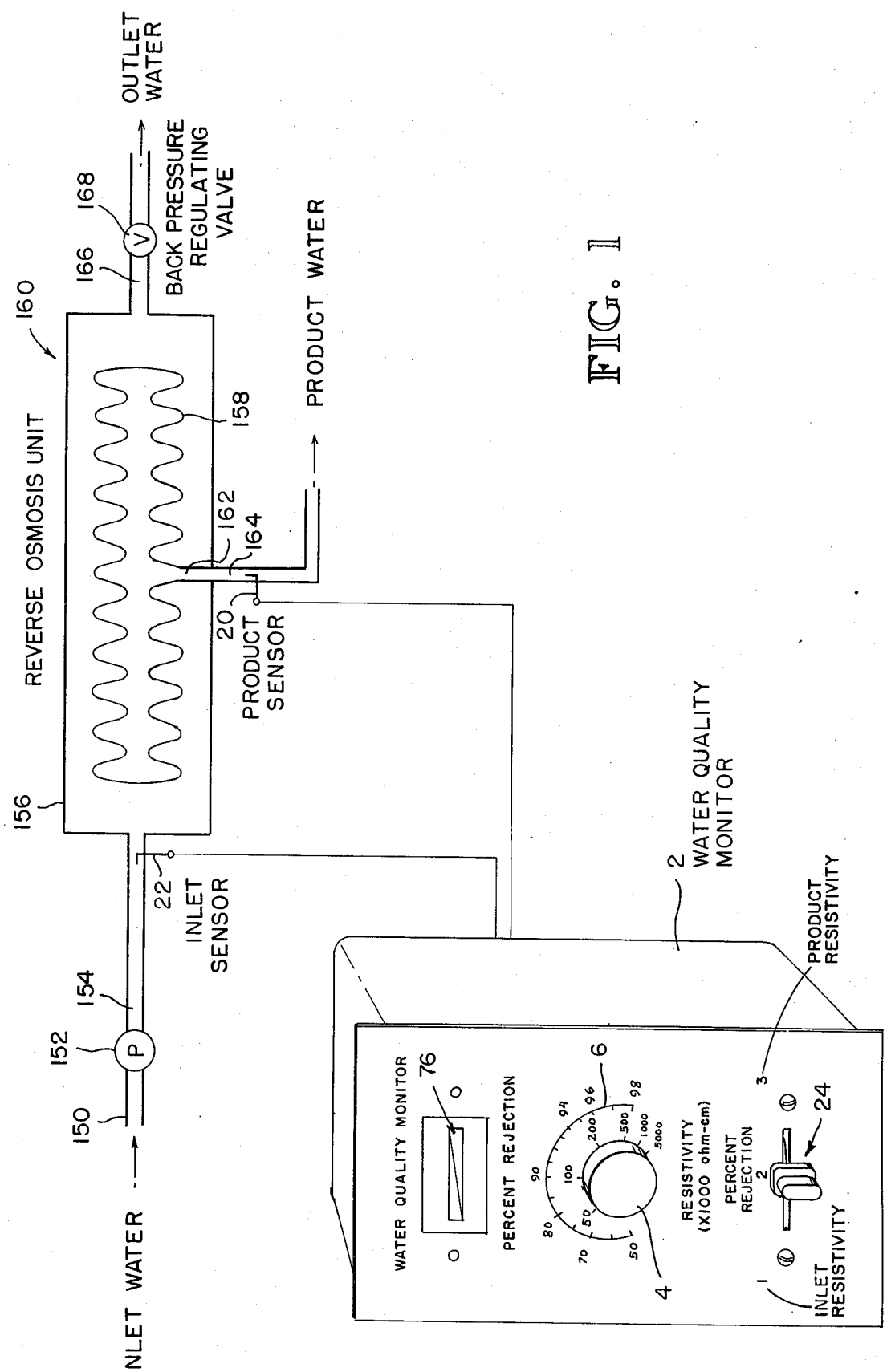
FIG. 1 is a schematic of a reverse osmosis water purification system showing the water quality monitor in operation.

Referring now to FIG. 1, untreated inlet water enters conduit 150 and is pressurized by pump 152. The inlet water then flows to a reverse osmosis unit 160 through conduit 154, containing a resistivity sensor 22 which measures the ion concentration of the inlet water.

The reverse osmosis unit 160 comprises a vessel 156 having three ports passing therethrough. Inside the vessel 156 is a closed envelope 158 fabricated from a semi-permeable membrane. The interior of the envelope 158 communicates with product conduit 164 through outflow port 162. The osmotic pressure produced by pump 152 causes the inlet water in the vessel 156 to pass through the semi-permeable membrane 158, leaving behind ionic material dissolved therein. Thus water entering the envelope 158 has a lower ion concentration than the inlet water. As inlet water passes through the membrane 158, leaving behind ions, the ion concentration of the water in the vessel tends to rise. To maintain a low ion concentration within the vessel 156, water continuously flows out of the vessel 156 through conduit 166. The flow of water through conduit 166 is controlled by a back pressure regulating valve to maintain a relatively high water pressure in the vessel 156.

As water passes into the envelope 158, purified water flows through the product conduit 164 where its ion concentration is measured by resistivity sensor 20.

Each of the resistivity sensors is connected to water quality monitor 2. A knob 4 is provided which is rotated to balance an internal wheatstone bridge. When the bridge is balanced, the darkened area of the meter 76 will be equal to the light area.

At that time, if the switch 24 is in its center position, the position of the knob 4 relative to the scale 6 will indicate the percentage of ions in the product water which have been rejected from the inlet water by the reverse osmosis unit 160. As will be explained hereinafter, this is expressed as "percent rejection." For example, if the inlet water has an ion concentration of 10 parts per million (p.p.m.) and the product water has an ion concentration of 1 p.p.m., the reverse osmosis unit 160 has rejected 90% of the ions present in the inlet water. Thus the percent rejection is 90.

If the switch 24 is placed in either the left or right position, the position of the knob 4 relative to the scale 6 when the bridge is balanced will indicate the resistivity of the inlet water or the product water. The resistivity can then be converted into ion concentration in a known manner.

Over the range of interest for water purification purposes, resistivity (R), expressed in ohm-centimeters, varies with the total dissolved metallic ion concentration (C), expressed as parts per million (p.p.m.) or milligrams per liter (mg./l.), in accordance with the equation:

$$RC = 4 \times 10^5 \qquad (1)$$

Equation 1 approximates the relation between resistance and ion concentration for nonvalent ions, such as sodium chloride, at 25° C. A measure of performance for reverse osmosis water purification systems is "percent rejection," which is the percentage of ions in the inlet water that are removed and do not appear in the product water. This can be expressed as:

$$\% \text{ rejection} = 100 \left( \frac{C_{in} - C_{out}}{C_{in}} \right) = 100 \left( 1 - \frac{C_{out}}{C_{in}} \right) \qquad (2)$$

It can be seen from equation 1 that $$C_{in} = \frac{4(10^5)}{R_{in}}$$

and that $$C_{out} = \frac{4(10^5)}{R_{out}}.$$

It follows that:

$$\% \text{ rejection} = 100 \left(1 - \frac{4(10^5)}{R_{out}} \times \frac{R_{in}}{4(10^5)}\right) = 100 \left(1 - \frac{R_{in}}{R_{out}}\right) \qquad (3)$$

Figure 2:
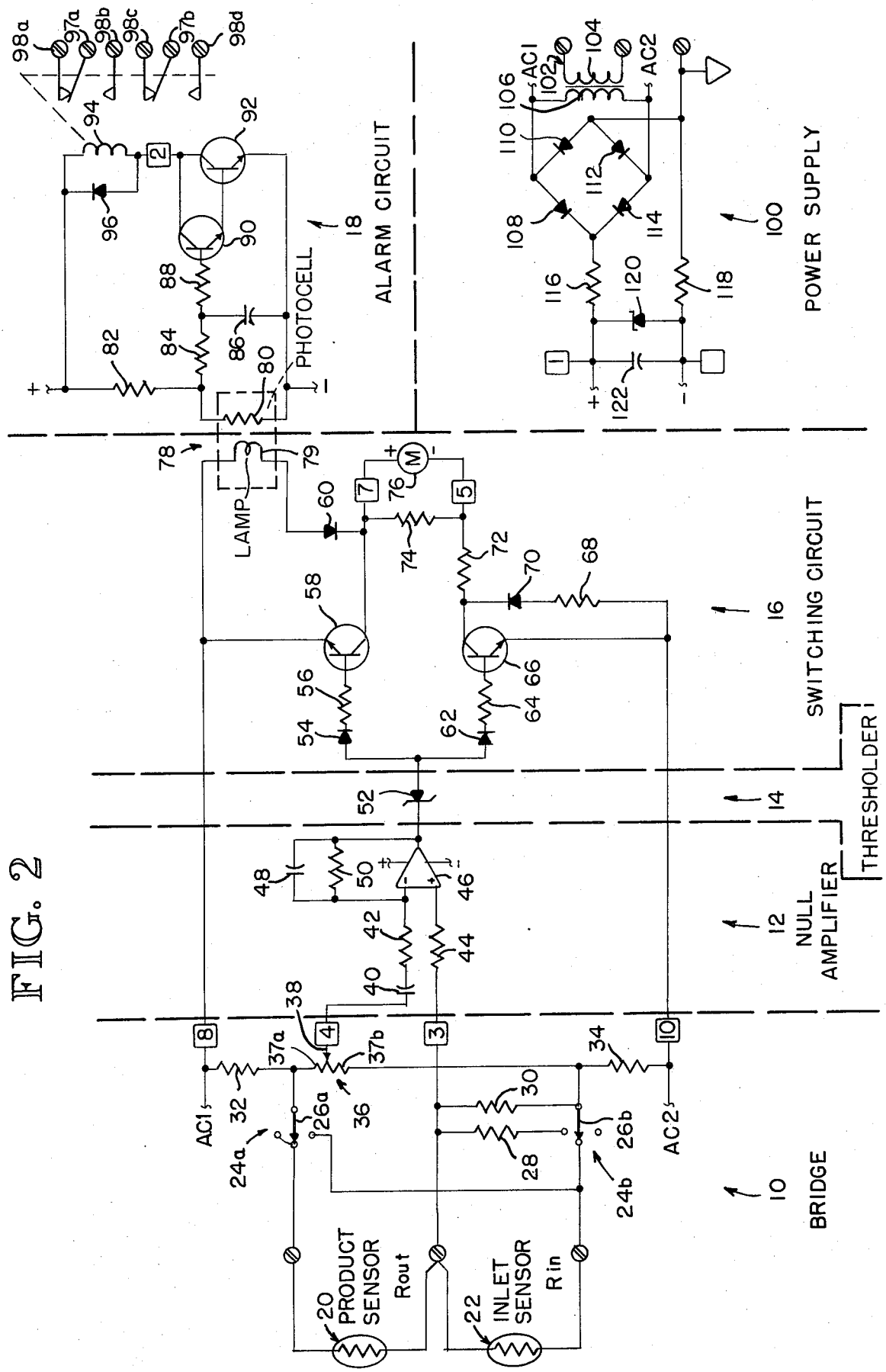
FIG. 2 is a schematic showing the circuit used in the preferred embodiment of the water quality monitor of the present invention.

Referring now to FIG. 2, a wheatstone bridge 10 is formed from output sensor 20, input sensor 22 and the resistances on either side of the wiper 38 of potentiometer 36. When the bridge 10 is balanced, $$\frac{R_{out}}{R_{in} + R_{out}}$$

will equal potentiometer resistance 37a divided by resistance 37a plus 37b. In a potentiometer having a rotatable wiper, the divider ratio 37a divided by 37a plus 37b is proportional to the rotation of the wiper blade divided by the total rotation. Thus:

$$\frac{\alpha}{\alpha T} = \frac{R_{out}}{R_{in} + R_{out}} \qquad (4)$$

where $\alpha$ is the rotation from CCW and $\alpha T$ is the total potentiometer rotation.

The resistivity sensor scale constants should be selected so that $\alpha/\alpha T$ is equal to 0.5 at the midpoint of the range of percent rejection. Since reverse osmosis water purification systems will normally remove between 85–95% of the metallic ions dissolved in water, $\alpha/\alpha T$ should equal 0.5 when the percent rejection is equal to 90%. With a percent rejection of 90%, the concentration of ions in the product water will be 1/10 the concentration of ions in the inlet water. In order to have $\alpha/\alpha T$ equal 0.5, $R_{in}$ would have to equal $R_{out}$ at 90% rejection. Thus, resistivity sensors must be used with scale constants in the ratio of 10:1 so that the product sensor will have a resistance of 1/10 the resistivity measured and the inlet sensor will have a resistance equal to the resistivity measured. The angular position of the balancing potentiometer 36 is compared against a fixed scale calibrated in percent rejection with a 90% rejection at the center point.

When the switch 24 is set to measure resistivity directly, a precision reference resistor is substituted for one sensor. Since the sensors used with the monitor have a resistance ratio of 10:1, the resistors used for reference must also have a 10:1 resistance ratio.

The circuitry used to implement the measurement and monitor function is shown in FIG. 2. With function switch 24 at its center position, the wheatstone bridge 10 has two legs formed by output sensor 20 and product sensor 22. The remaining two legs of the bridge 10 are formed by resistors 37a and 37b on either side of the wiper 38 of potentiometer 36. The bridge is powered by two oppositely phased AC signals, AC1 and AC2. The potentiometer 36 is adjusted so that resistance 37b divided by resistance 37a plus 37b will be equal to $R_{in}$ divided by $R_{in}$ plus $R_{out}$, thus making the voltage at both inputs to amplifier 46 equal. The angular position of the wiper 38 on potentiometer 36 is then used to indicate the percent rejection.

The null amplifier 12 is a high-gain operational amplifier, such as the uA741 sold by Fairchild Semi-Conductors, Inc. The non-inverting input to amplifer 46 is driven by one output of the bridge 10 through resistor 44. The other output of the bridge 10 drives the summing junction of amplifier 46 through capacitor 40 and resistor 42. Capacitor 40 prevents the amplifier 46 from responding to DC voltages sometimes generated by sensors 20 and 22. The break point of the input circuits 40 and 42 is at approximately 40 cycles, thereby insuring a flat frequency response at 60 Hz., which is the frequency of AC signals AC1 and AC2. The parallel combination of capacitor 48 and resistor 50 in the feedback path rolls off the amplifier gain at approximately 2 kHz. to maintain the stability of the amplifier 46. In operation, oppositely phased 60 Hz. sign waves are applied to AC1 and AC2. Depending upon the balance of the bridge, a signal, either in phase or out of phase, will appear at the non-inverting input to amplifier 46. If the bridge has been previously balanced and the resistance of output sensor 20 decreases, the signal at the non-inverting input to amplifier 46 will be identical in phase to AC1. Similarly, if the resistance of input sensor 22 decreases relative to the resistance of output sensor 20, the signal at the non-inverting input to amplifier 46 will be identical in phase to AC2. The signal at the non-inverting input to amplifier 46 will be inverted by amplifier 46 and applied to the cathode of zener diode 52, which serves as a thresholder.

The anode of zener diode 52 is connected to a switching circuit 16 which consists of two current paths. The first current path is from AC1 through lamp 79, diode 60, resistor 74 (in parallel with meter 76), resistor 72 and transistor 66. The second current path is from AC2 through resistor 68, diode 70, resistor 72, resistor 74 (in parallel with meter 76) and transistor 58 to AC1. The bases of transistors 58 and 66 are driven in common by the anode of zener diode 52. When a signal appears at the output of amplifier 46 in excess of the breakdown voltage of the zener diode 52, base emitter current will flow in the transistor having its emitter connected to the AC signal having a phase opposite to the phase of the AC signal at the output of the amplifier 46. Collector current will then flow through the diode of the other transistor diode pair and through the common load. Because of the presence of diodes 54 and 62, current will flow only during the positive excursion of the signal. Thus, for example, when a signal in phase with AC2 appears with sufficient magnitude at the output of amplifier 46, current will flow through diode 54, resistor 56 and the base emitter junction of transistor 58 to AC1, which has a polarity opposite from the polarity of the signal at the output of amplifier 46. Transistor 58 will then saturate, allowing current to flow through resistor 68, diode 70, resistor 72 and the meter 76, in parallel with resistor 74, to AC1. Similarly, when the signal at the output of amplifier 46 has the same phase as AC1 and is positive of a sufficient magnitude, current will flow through diode 62, resistor 64 and the base emitter junction of transistor 66. Transistor 66 will then be saturated, allowing current to flow through lamp 79, diode 60, meter 76, in parallel with resistor 74, and resistor 72 to AC2. Note that current will flow through meter 76 in opposite directions, depending upon which transistor is saturated. While the indicating device shown in FIG. 2 comprises a meter, it will be apparent to one skilled in the art that other indicators can be advantageously used. For example, a light-emitting diode (LED) may be placed in each of the current paths. When both of the LED's are equally illuminated, the bridge 10 will be balanced.

When transistor Q1 is saturated, thereby indicating a decrease in the resistance of output sensor 20, and hence an increase in ion concentration at the output, alarm circuit 18 will be driven through optical isolator 78. When the lamp 79 of optical isolator 78 is illuminated, the resistance of photo-cell 80 drops to discharge capacitor 86 through resistor 84. Capacitor 86 had previously been charged by current flowing through resistors 82 and 84. After capacitor 86 has been sufficiently discharged, the voltage at the input to transistors 90 and 92, arranged as a Darlington pair, will drop to cut off the transistors 90 and 92 to de-energize relay winding 94, thereby connecting contact 97a to 98b and 97b to 98d to actuate an external alarm.

Although the circuit shown in FIG. 2 represents the preferred embodiment, it is clear that the circuit can be modified to some extent without departing from the inventive concept of the water quality monitor. For example, transistors 58 and 66 can be PNP-type transistors, in which case zener diode 52 and diodes 54, 62, 60 and 70 would be reversed and the aforementioned operating potentials would be of the opposite polarity. Similarly, the collectors, instead of the emitters, of transistors 58 and 66 could be connected to AC signals AC1 and AC2, in which case the voltage at the base of transistor 58 would be compared to AC2, and the voltage at the base of transistor 66 would be compared at AC1.

In summary, when the potentiometer 36 is set at null, the voltage at the output of amplifier 46 is zero. At this time, both transistors 58 and 66 will be off, transistors 90 and 92 will be on, and relay 94 will be energized. If the resistivity measured by the output center 20, relative to the resistivity measured by the input sensor 22, increases, the AC signal at the non-inverting input to amplifier 46, as well as the output of the amplifier 46, will be an AC signal in phase with AC2. When the unbalance causes the voltage at the output of amplifier 46 to exceed the breakdown voltage of zener diode 52, transistor 58 saturates on the negative cycle of AC1. This will cause the meter to deflect to the right, indicating that the resistivity ratio, and hence the percent rejection, exceeds the percent rejection setting on the potentiometer 36.

The circuit performs in a similar manner if the function switch 24 is set to either the first or third position. In this mode, the only difference will be that the sensor being measured will be compared to a fixed value reference resistor. Thus the bridge 10 will be unbalanced by a change in the absolute resistivity value and not a change in the resistivity ratio as when the function switch 24 is in its second position. Thus, when function switch 24b is in its first position, output sensor 20 will be in one leg of the bridge and resistor 28 will be in the other leg. In this mode, when the bridge is balanced, the position of the wiper 38 will indicate the resistivity of the product sensor 20 and, therefore, the ion concentration of the product water flowing out of the purification system. Similarly, when the function switch 24 is in its third position, inlet sensor 22 and resistor 30 will form two legs of the bridge and the position of wiper 38 at no point will indicate the concentration of ions dissolved in water flowing into the purification system. Since the scale factor of the inlet sensor 22 is ten times greater than the scale factor of the product sensor 20, the fixed resistance 28 compared to the output sensor 20 is 1/10 the fixed resistance 30 compared to the input sensor 22.

The oppositely phased AC signals, AC1 and AC2, as well as the power for amplifier 46, are generated by power supply 100. The primary windings 104 of a transformer 102 are connected to a 60 Hz., 120 volt power source. The secondary windings 106 drive a conventional bridge rectifier formed from diodes 108, 110, 112 and 114. The rectifier output is regulated by zener diode 120 and filtered by capacitor 122 after passing through dropping resistors 116 and 118. Thus the voltage on capacitor 122 is a relatively constant voltage suitable for powering amplifier 46.

The embodiments of the invention in which an exclusive property or privilege is claimed are defined as follows:

1. A phase sensitive null detector receiving a null error signal from a wheatstone bridge, comprising:
    means for generating first and second AC signals having a predetermined phase difference, said AC signals supplying power to said bridge through first and second AC signal lines;
    a first current path for allowing current to flow from said first AC signal line to said second AC signal line;
    a second current path for allowing current to flow from said second AC signal line to said first AC signal line;
    indicating means for indicating a comparison between the current through said first current path and the current through said second current path;
    means responsive to a difference in voltage between said null error signal and one of said AC signals for allowing current to flow in said first current path; and
    means responsive to a difference in voltage between said null error signal and the other of said AC signals for allowing current to flow in said second current path.

2. A null detector as in claim 1 wherein:
    said first current path and said means for allowing current to flow in said first current path comprise:
    a first transistor connecting said first AC signal line to a first terminal of said indicating device and having its base driven by said null error signal;
    a first diode connecting a second terminal of said indicating device to said second AC signal line, said first diode positioned to allow current to flow in sequence through said first transistor, said indicating device and said first diode;
    said second current path and said means for allowing current to flow in said second current path comprise:
    a second transistor connecting said second AC signal line to a fourth terminal of said indicating device and having its base driven by said null error signal;
    a second diode connecting a third terminal of said indicating device to said first AC signal line, said second diode being positioned to allow current to flow in sequence through said second transistor, said indicating device and said second diode.

3. A null detector as in claim 2 wherein said means for allowing current to flow in said first and second current paths is responsive to a signal generated by thresholding said error signal.

4. A null detector as in claim 2 wherein said indicating device is a meter and said first terminal is connected to said third terminal and said second terminal is connected to said fourth terminal.

5. A null detector as in claim 2 wherein said indicating device is at least one light-emitting diode.

6. A null detector as in claim 2 wherein said means for generating a null error signal includes means for reducing the ratio of null error voltage to differential output voltage from said bridge when said differential output voltage is below a predetermined frequency.

7. In a system for monitoring the performance of a reverse-osmosis water purifier wherein a first sensor measures the resistivity of product water leaving said purifier and a second sensor measures the resistivity of water entering said purifier, a phase-sensitive null detector comprising:
    means for generating first and second AC signals on first and second AC signal lines, said AC signals having a predetermined phase difference;
    a potentiometer having a first potentiometer resistance on one side of a potentiometer wiper and a second potentiometer resistance on the other side of said potentiometer wiper;
    a wheatstone bridge having a first leg formed by said first sensor, a second leg formed by said second sensor, a third leg formed by said first potentiometer resistance and a fourth leg formed by said second potentiometer resistance, said bridge being powered by said first AC signal at the junction of said first sensor and said first potentiometer resistance and by said second AC signal at the junction of said second sensor and said second potentiometer resistance;
    means for generating a null error signal having a value proportional to the difference between the voltage on said potentiometer wiper and the voltage at the junction of said first and second sensors;
    a first current path for allowing current to flow from said first AC signal line to said second AC signal line;
    a second current path for allowing current to flow from said second AC signal line to said first AC signal line;
    indicating means for indicating a comparison between the current through said first current path and the current through said second current path;
    means responsive to a difference in voltage between said first error signal and one of said AC signals for allowing current to flow in said first current path; and means responsive to a difference in voltage between said null error signal and the other of said AC signals for allowing current to flow in said second current path.

8. A null detector as in claim 7, further including means for alternately replacing each of said sensors with a fixed resistance.

9. A null detector as in claim 7, further including means for indicating the angular position of said potentiometer wiper and a fixed scale positioned adjacent said indicator calibrated in rejection percentage whereby the angular position of said potentiometer wiper relative to said fixed scale when the bridge is balanced will denote the percentage of metallic ions removed from the water passing through said reverse osmosis water purifier.

10. A null detector as in claim 7, further including means for actuating an alarm when said bridge becomes unbalanced by a predetermined value.

11. A null detector as in claim 10 wherein said means for allowing current to flow in said first and second current paths is responsive to a signal generated by thresholding said null error signal and said means for actuating an alarm measures the quantity of current flow through one of said current paths and is actuated by current flow of a predetermined quantity.

12. A system for monitoring the performance of a reverse-osmosis water purifier wherein a first sensor measures the resistivity of product water leaving said purifier and a second sensor measures the resistivity of water entering said purifier, said system comprising:
- means for providing first and second, oppositely-phased AC signals on respective first and second AC signal lines;
- a potentiometer having a potentiometer wiper movable with respect to a fixed scale, said fixed scale having indicia corresponding to the impurity concentration of said first sensor with respect to the impurity concentration at said second sensor;
- a wheatstone bridge powered by said first and second AC signals, said bridge having legs formed by said first and second sensors and said potentiometer such that when said bridge is balanced, the position of said potentiometer wiper with respect to said scale indicates the impurity concentration of said first sensor with respect to the impurity concentration at said second sensor; and
- phase-sensitive discriminator means comparing said wheatstone bridge output with said first and second AC signals and providing an indication thereof such that quadrature components at the bridge output caused by the capacitive reactance of said sensors are substantially eliminated from said comparison when the impurity concentration at said first sensor with respect to the impurity concentration at said second sensor corresponds to the relative impurity concentration indicated by the position of said potentiometer wiper with respect to said scale.

13. The monitoring system of claim 12 wherein said discriminator means includes a meter having a pointer which is deflected in one direction responsive to said bridge output being in phase with said first AC signal, and is deflected in the opposite direction responsive to said bridge output being in phase with said second AC signal such that a neutral position of said pointer indicates that said bridge is balanced responsive to the impurity concentration at said first sensor with respect to the impurity concentration at said second sensor being substantially equal to the relative impurity concentrations corresponding to the position of said potentiometer wiper with respect to said fixed scale.

14. The monitoring system of claim 13 wherein said discriminator means comprise:
- a first current path for allowing current to flow from said first AC signal line to said second AC signal line;
- a second current path for allowing current to flow from said second AC signal line to said first AC signal line,
- means responsive to the difference in voltage between bridge output and one of said AC signals for allowing current to flow in said first current path; and
- means responsive to the difference in voltage between said bridge output and the other of said AC signals for allowing current to flow in said second current path.

15. The monitoring system of claim 12 wherein said discriminator means includes alarm means actuated when the component of said bridge output in phase with one of said AC signals exceeds a predetermined value thereby indicating a predetermined deviation from the relative impurity concentrations at said first and second sensors corresponding to the position of said potentiometer wiper with respect to said fixed scale.

16. A system for monitoring the performance of a reverse-osmosis water purifier wherein a first sensor measures the resistivity of product water leaving said purifier and a second sensor measures the resistivity of water entering said purifier, said system comprising:
- a potentiometer having a potentiometer wiper movable with respect to a fixed scale, said fixed scale having indicia corresponding to the impurity concentration at said first sensor with respect to the impurity concentration at said second sensor;
- a wheatstone bridge powered by an AC signal, said bridge having legs formed by said first and second sensors and said potentiometer such that when said bridge is balanced the position of said potentiometer wiper with respect to said scale indicates the impurity concentration at said first sensor with respect to the impurity concentration at said second sensor; and
- phase-sensitive discriminator means comparing the output of said wheatstone bridge with said AC signal and providing an indication thereof such that quadrature components of said bridge output caused by the capacitive reactance of said sensors are substantially eliminated from said comparison when the impurity concentration at said first sensor with respect to the impurity concentration at said second sensor corresponds to the relative impurity concentration indicated by the position of said potentiometer wiper with respect to said scale.

17. The system of claim 16 wherein said discriminator means further includes alarm means actuated when the component of said said bridge output in phase with said AC signal is a predetermined value thereby indicating a predetermined deviation from the relative impurity concentration corresponding to the position of said potentiometer wiper with respect to said scale.

* * * * *